(12) United States Patent
Khamis et al.

(10) Patent No.: US 12,115,995 B2
(45) Date of Patent: Oct. 15, 2024

(54) IN-VEHICLE MULTIMODAL VIOLENCE DETECTION FOR SHARED VEHICLES AND SELF-DRIVING SHUTTLES

(71) Applicant: GM Global Technology Operations LLC, Detroit, MI (US)

(72) Inventors: Alaa M. Khamis, Courtice (CA); Wei Tong, Troy, MI (US); Sai Vishnu Aluru, Commerce Township, MI (US); Upali P. Mudalige, Rochester Hills, MI (US); Sravan Daruri, Walled Lake, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 266 days.

(21) Appl. No.: 17/829,643

(22) Filed: Jun. 1, 2022

(65) Prior Publication Data

US 2023/0391344 A1 Dec. 7, 2023

(51) Int. Cl.
*B60W 40/08* (2012.01)
*A61B 5/00* (2006.01)
(Continued)

(52) U.S. Cl.
CPC ...... *B60W 40/08* (2013.01); *B60W 30/18109* (2013.01); *G06V 10/12* (2022.01);
(Continued)

(58) Field of Classification Search
CPC ........... B60W 40/08; B60W 30/18109; B60W 2040/089; G06V 10/12; G06V 20/59;
(Continued)

(56) References Cited

U.S. PATENT DOCUMENTS 10,147,325 B1 * 12/2018 Copeland ............. G06Q 20/145
10,768,620 B1 * 9/2020 Tran .................... A61B 5/02416
(Continued)

OTHER PUBLICATIONS

Jiang, Zhuangyi, et al. Mixed frame-/event-driven fast pedestrian detection. In: 2019 International Conference on Robotics and Automation (ICRA). IEEE, 2019. S. 8332-8338. Aufgerufen Ober: URL:https://ieeexplore. ieee.org/abstracUdocu menU8793924.
(Continued)

*Primary Examiner* — Kurt Philip Liethen
(74) *Attorney, Agent, or Firm* — Vivacqua Crane, PLLC (57) ABSTRACT

An in-vehicle violence detection system includes a speech and non-speech audio recognition module capturing occupant threat words and non-speech audio events. In-vehicle accelerometers generate data analyzed in a shaking movement recognition module. A heart rate and breathing rate detection module measures physiological changes in occupant heart rates and breathing rhythms. An in-vehicle semantic scene recognition module analyzes occupant non-verbal interactions. Occupant threat indicators including an audible threat indicator are generated by the speech and non-speech audio event recognition module. Visual threat indicators are generated by the in-vehicle semantic scene recognition module. Physiological threat indicators are generated by the heart rate and breathing rate detection module. Vibration-based threat indicators are generated by the shaking movement recognition module. The four threat indicators are fused to estimate a threat level, consolidated by incorporating contextual information including a vehicle location and time. Different actions are taken based on the consolidated threat level.

19 Claims, 3 Drawing Sheets

(51) Int. Cl.
A61B 5/0205 (2006.01)
A61B 5/16 (2006.01)
B60W 30/18 (2012.01)
G06V 10/12 (2022.01)
G06V 20/59 (2022.01)
G06V 20/70 (2022.01)
G10L 15/22 (2006.01)
G10L 25/63 (2013.01)

(52) U.S. Cl.
CPC .............. G06V 20/59 (2022.01); G06V 20/70 (2022.01); G10L 15/22 (2013.01); G10L 25/63 (2013.01); *A61B 5/0205* (2013.01); *A61B 5/165* (2013.01); *A61B 5/6893* (2013.01); *B60W 2040/089* (2013.01)

(58) Field of Classification Search
CPC ...... G06V 20/70; G06V 40/70; G06V 20/597; G10L 15/22; G10L 25/63; G10L 15/26; G10L 25/51; A61B 5/0205; A61B 5/165; A61B 5/6893; A61B 5/18
See application file for complete search history.

(56) References Cited

U.S. PATENT DOCUMENTS

| | | | |
|---|---|---|---|
| 11,080,987 B2* | 8/2021 | Butler | G08B 27/001 |
| 11,887,383 B2* | 1/2024 | Turcot | G06V 20/59 |
| 11,922,787 B1* | 3/2024 | Barcia | G06V 10/70 |
| 2013/0070928 A1* | 3/2013 | Ellis | H04R 25/30 381/56 |
| 2016/0189517 A1* | 6/2016 | Weast | G08B 21/0423 340/573.1 |
| 2017/0330044 A1* | 11/2017 | Telpaz | B60K 35/10 |
| 2018/0143635 A1* | 5/2018 | Zijderveld | A61B 5/165 |
| 2019/0016343 A1* | 1/2019 | Allen | G06Q 50/40 |
| 2021/0009140 A1* | 1/2021 | Brooks | B60W 60/0059 |
| 2021/0182617 A1* | 6/2021 | Kondo | G06V 40/23 |
| 2021/0206268 A1* | 7/2021 | Bayer | B60K 35/00 |
| 2021/0250470 A1* | 8/2021 | Xiang | G06V 40/162 |
| 2021/0397858 A1* | 12/2021 | Buerkle | B60W 60/0016 |
| 2023/0419690 A1* | 12/2023 | Tong | G06T 7/292 |

OTHER PUBLICATIONS

Posch, Christoph; Matolin, Daniel; Wohlgenannt, Rainer. A QVGA 143 dB dynamic range frame-free PWM image sensor with lossless pixel-level video compression and time-domain CDS. IEEE Journal of Solid-State Circuits, 2010, 46. Jg., Nr. 1, S. 259-275. Aufgerufen Ober: URL:https://ieeexplore. ieee.org/abstracUdocu menU5648367.

* cited by examiner

IN-VEHICLE MULTIMODAL VIOLENCE DETECTION FOR SHARED VEHICLES AND SELF-DRIVING SHUTTLES

INTRODUCTION

The present disclosure relates to an automobile vehicle abnormal or threat situation recognition system.

Shared mobility technology has matured significantly, as is evident by the appearance of commercially available shared mobility services such as car sharing, ridesharing, ride-hailing and ride-sourcing. Shared autonomous vehicles (SAVs) and pooled shared autonomous vehicles (PSAVs) are also quickly emerging. Sharing a ride with a stranger in a shared autonomous vehicle (SAV) could present risks to a users' personal physical and emotional safety. Perception of crowding and violations of personal space may also be likely when passengers ride-share or ride-pool with strangers.

Thus, while current shared and pooled shared autonomous automobile vehicles achieve their intended purpose, there is a need for a new and improved autonomous automobile vehicle in-vehicle multimodal violence detection system.

SUMMARY

According to several aspects, an in-vehicle multimodal violence detection system includes a speech and non-speech audio event recognition module capturing threat words and non-speech audio events of occupants of an automobile vehicle. Multiple in-vehicle accelerometers generate in-vehicle accelerometer data analyzed in a shaking movement recognition module. A heart rate and breathing rate detection module measures physiological changes in heart rates and breathing rhythms of the occupants. An in-vehicle semantic scene recognition module captures and analyzes non-verbal interactions between the occupants. One or more occupant threat indicators include an audible threat indicator are generated by the speech and non-speech audio event recognition module. A visual threat indicator is generated by the in-vehicle semantic scene recognition module. A physiological threat indicator is generated by the heart rate and breathing rate detection module. A vibration-based threat indicator is generated by the shaking movement recognition module.

In another aspect of the present disclosure, a priori knowledge defining a history record of violence is applied to determine a threat level.

In another aspect of the present disclosure, an outside source provides the a priori information.

In another aspect of the present disclosure, the a priori information includes an area of travel wherein known violence has occurred and a past history record of different "normal" versus "threat" behavioral events.

In another aspect of the present disclosure, a picture compilation module identifies vectors combining an output signal from the speech and non-speech audio event recognition module, the shaking movement recognition module, the heart rate and breathing rate detection module and the in-vehicle semantic scene recognition module and assigns predetermined thresholds distinguishing between a normal event and a threat event.

In another aspect of the present disclosure, a threat evaluation module analyzing the threat event using audible, visual, physiological and vibration-based indicators, and an a priori knowledge including a history record of violence and contextual information having a location and a time of day to determine a threat level.

In another aspect of the present disclosure, a threat assessment unit receives the threat level, confirms if an active threat is present and generates an active threat signal.

In another aspect of the present disclosure, after generating the active threat signal a threat confirmation request is generated and forwarded to a threat timer unit.

In another aspect of the present disclosure, a confirmation request is visually and audibly presented to the occupants and a predetermined time interval is allowed for at least one of the occupants to confirm if the active threat is present in the automobile vehicle is set. A threat level determination unit is initiated by a time interval time-out signal if the predetermined time interval is exceeded prior to receiving a response from any one of the occupants.

In another aspect of the present disclosure, an active threat signal is generated and forwarded to the threat level determination unit if any one of the occupants confirm that an active threat is present. The threat level determination unit identifies if the active threat should be categorized as one of a "low threat", a "medium threat" or a "high threat", wherein: identification of the "low threat" activates a vehicle horn and a vehicle warning flasher; identification of the "medium threat" activates the vehicle horn and the vehicle warning flasher and activates a vehicle brake assist system and notification of the medium threat to an outside source; and identification of the "high threat" activates the vehicle horn and the vehicle warning flasher, activates the vehicle brake assist system and forwards a request to the outside source to initiate an emergency assistance request.

According to several aspects, a method to perform in-vehicle multimodal violence detection includes: capturing threat words and non-speech audio events of occupants of an automobile vehicle using a speech and non-speech audio event recognition module; collecting in-vehicle accelerometer data; measuring sudden physiological changes in heart rates and breathing rhythms of the occupants in a heart rate and breathing rate detection module; capturing and analyzing non-verbal interactions between the occupants using an in-vehicle semantic scene recognition module; generating one or more threat indicators including audible, visual, physiological and vibration-based indicators.

In another aspect of the present disclosure, the method includes applying a priori knowledge including a history record of violence to determine a threat level.

In another aspect of the present disclosure, the method includes applying contextual information including a vehicle location and a time of day from the a priori knowledge.

In another aspect of the present disclosure, the method includes incorporating ride information and occupant information from a booking database and analyzing the ride information and the occupant information to distinguish differences between the occupants.

In another aspect of the present disclosure, the method includes identifying shaking movements of the occupants of the automobile vehicle using the in-vehicle accelerometer data.

In another aspect of the present disclosure, the method includes applying inarticulate sounds and sounds accompanying threat or abnormal behaviors including shouting, screaming, crying and glass breaking as audio-based threat indicators.

In another aspect of the present disclosure, the method includes analyzing the one or more occupant threat indicators in a multimodal threat evaluation module.

According to several aspects, a method to perform in-vehicle multimodal violence detection includes: capturing threat words and non-speech audio events of occupants of an autonomous automobile vehicle using a speech and non-speech audio event recognition module; analyzing in-vehicle accelerometer data in a shaking movement recognition module; measuring sudden physiological changes in heart rates and breathing rhythms of the occupants in a heart rate and breathing rate detection module; capturing and analyzing non-verbal interactions between the occupants using an in-vehicle semantic scene recognition module; generating one or more occupant threat indicators including audible, visual, physiological and vibration-based indicators; and identifying vectors combining an output signal from the speech and non-speech audio event recognition module, the shaking movement recognition module, the heart rate and breathing rate detection module and the in-vehicle semantic scene recognition module and assigning predetermined thresholds distinguishing between a normal event and a threat event in a picture compilation module.

In another aspect of the present disclosure, the method includes: collecting output signals of multiple in-vehicle cameras positioned in the autonomous automobile vehicle; identifying if any one of the multiple in-vehicle cameras is covered in a camera assessment unit; and generating an audio pulse signal by the camera assessment unit to notify the occupants of the autonomous automobile vehicle to uncover a covered one of the any one of the multiple in-vehicle cameras.

In another aspect of the present disclosure, the method includes: identifying by receipt of an occupant status signal forwarded to an occupant confirmation unit if two or more occupants are present in the autonomous automobile vehicle; actuating operation of a ride type identification unit, wherein: if a "hailing ride type" signal is generated by the ride type identification unit a first program assumption is made that all of the occupants present in the autonomous automobile vehicle are known to each other and that no threats will later occur; or if a "sharing ride type" signal is generated by the ride type identification unit a second program assumption is made that at least one of the occupants present in the autonomous automobile vehicle is not previously known to other ones of the occupants and that a potential therefore exists for the threat event to develop during subsequent operation of the autonomous automobile vehicle.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
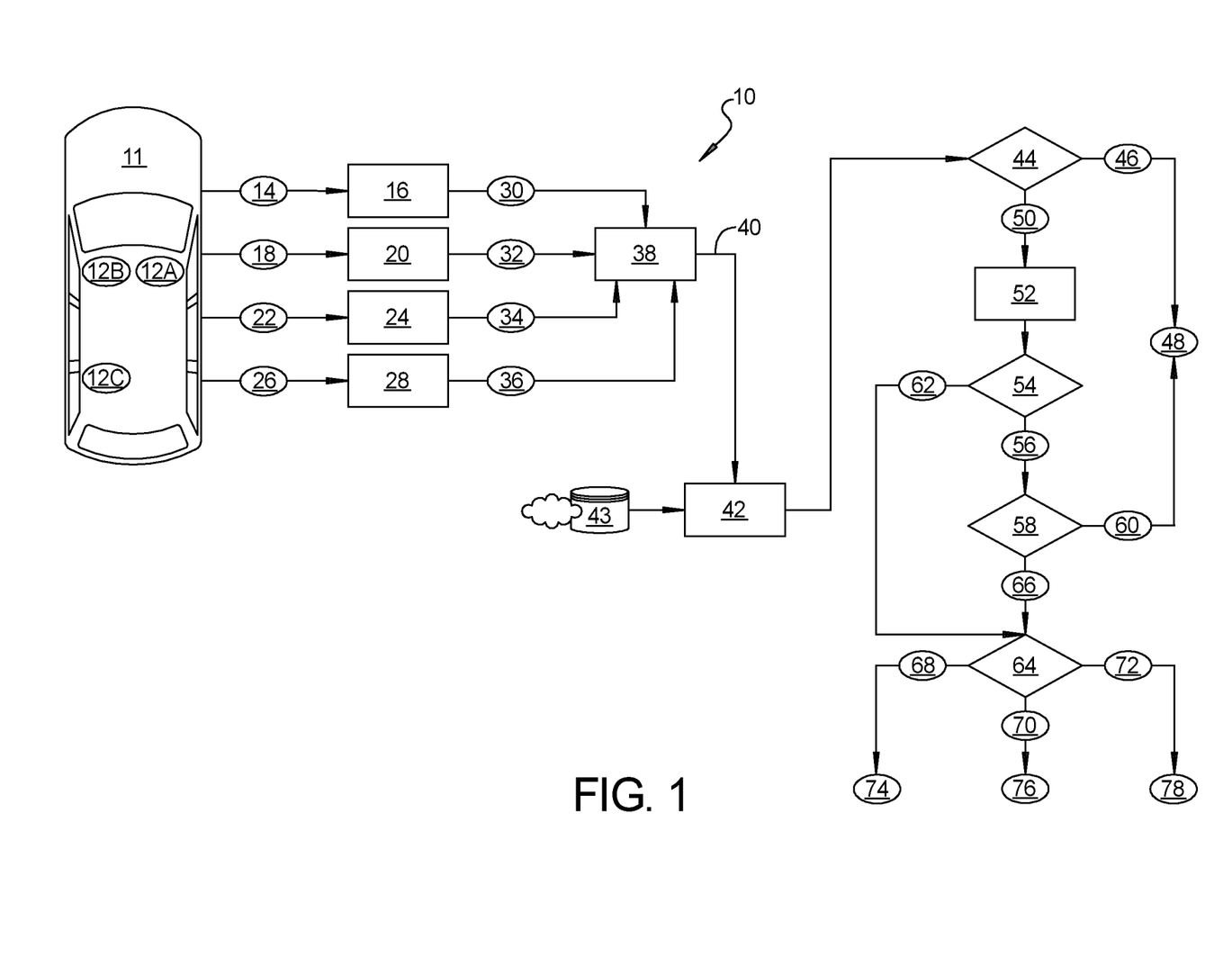
FIG. 1 is a system diagram of an in-vehicle multimodal violence detection system according to an exemplary aspect.

Referring to FIG. 1, an in-vehicle multimodal violence detection system 10 is provided with an automobile vehicle 11 including but not limited to an autonomous automobile vehicle including but not limited to shared autonomous vehicles (SAVs) and pooled shared autonomous vehicles (PSAVs). The in-vehicle multimodal violence detection system 10 provides multiple devices used for recognition of threats including audio threats, vibration-based threats, vision threats and physiological threats which may impact a vehicle occupant 12 such as a driver or operator occupant 12A, a front passenger occupant 12B and one or more rear passenger occupants 12C. As will be discussed below, identified threats may be characterized as low threats, medium threats and high threats, and threats may be further distinguished depending on an area of operation of the automobile vehicle 11.

The in-vehicle multimodal violence detection system 10 includes multiple in-vehicle microphones 14 which detect occupant speech and direct signals from the in-vehicle microphones 14 to a speech and audio event recognition module 16. The in-vehicle multimodal violence detection system 10 also includes multiple in-vehicle accelerometers 18 which detect occupant motion including occupant hand motion and head motion and direct signals and data from the in-vehicle accelerometers 18 to a shaking motion movement module 20. The shaking motion movement module 20 recognizes shaking movement using the in-vehicle accelerometer data, where shaking movement is defined as a vibration, an oscillation, or an abrupt motion defining an instantaneous or immediate motion.

Figure 2:
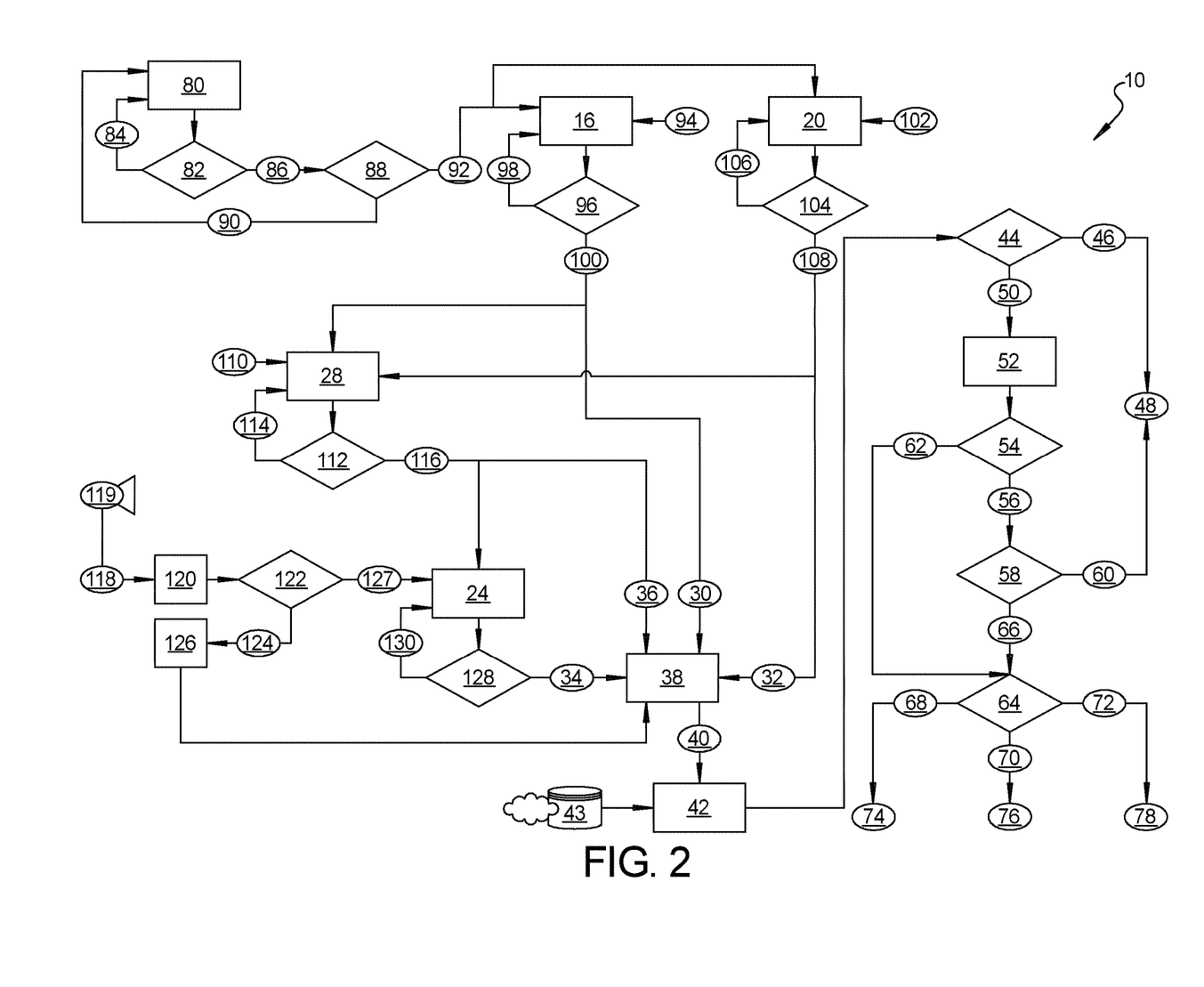
FIG. 2 is a flow diagram of method steps and components of the in-vehicle multimodal violence detection system of FIG. 1.

The in-vehicle multimodal violence detection system 10 also includes multiple in-vehicle cameras discussed in greater detail in reference to FIG. 2 which generate in-vehicle camera data 22 relating to occupant positions and movements over time and direct signals from the in-vehicle camera data 22 to an in-vehicle semantic scene recognition module 24. The in-vehicle semantic scene recognition module 24 captures and analyzes non-verbal interactions between vehicle occupants 12 to generate an occupant threat indicator.

The in-vehicle multimodal violence detection system 10 also includes one or more in-vehicle radar devices 26 which detect heart rates and breathing rates of the occupants 12 and direct signals from the in-vehicle radar devices 26 to a heart rate and breathing rate detection module 28. The heart rate and breathing rate detection module 28 analyzes occupants' sudden changes in heart rates and breathing rhythms.

The speech and audio event recognition module 16 analyzes patterns, volume, and the like of the detected occupant speech and generates audio-based threat indicators 30. The shaking motion movement module 20 analyzes acceleration, amplitudes and directions of occupant motions and generates vibration-based threat indicators 32. The in-vehicle semantic scene recognition module 24 analyzes differences in occupant positions or occupant head or limb positions over time as a changing semantic scene and generates vision-based threat indicators 34. The heart rate and breathing rate detection module 28 analyzes data generated by the in-vehicle radar devices 26 whose outputs are used to generate occupant physiological-based threat indicators 36.

The audio-based threat indicators 30, the vibration-based threat indicators 32, the vision-based threat indicators 34 and the physiological-based threat indicators 36 are forwarded to a picture compilation module 38. The picture compilation module 38 identifies vectors for the inputs which may for example combine a visual signal and an auditory signal and may assign predetermined thresholds to individual inputs to distinguish between "normal" events where some increased sound level will occur, or some increased vibration or motion may occur, differentiated from a "threat" event by one or more thresholds being applied. The picture compilation module 38 compiles one or more observation vectors 40 of the input data and the thresholds for transmission to a threat evaluation module 42. The threat evaluation module 42 analyzes threat situations using audible, visual, such as physiological and vibration-based indicators, and uses the a priori knowledge such as a history record of violence and contextual information such as location, time of the day and the like, to determine a threat level.

The threat evaluation module 42 receives the observation vectors 40 and augments this information with additional information to assist in differentiating "normal" events from "threat" events. For example, an outside source 43 such as a cloud-based system may provide a priori information such as an area of travel wherein known violence has occurred and a past history record of different "normal" versus "threat" behavioral events to use for comparison purposes against the present observation vectors 40. Contextual information may also be received from the outside source 43 which may include data distinguishing different areas the automobile vehicle 11 will travel through and rates of or different types of violence that may occur at different times of day or night. For example, a high crime area may have abnormally high rates of robbery after 10:00 pm, or areas may be historically deemed safe during an early morning or afternoon period. The outside source 43 may also provide occupant information from a SAV booking database, for example when a ride-share or ride-pool request is made by one of the occupants 12. The threat evaluation module 42 uses the above input, saved and collected information to identify potential threats for further analysis and confirmation.

It is noted the outside source 43 may further include a monitoring and reporting system such as OnStar® which may further result in communication of the threat assessment together with emergency contact and identification information related to the automobile vehicle 11 being forwarded to an emergency service such as a 911 operator.

The threat evaluation module 42 forwards potential threat information to a threat assessment unit 44. If the threat assessment unit 44 confirms there is no active threat a first no-threat signal 46 is generated and saved at a "nothing abnormal" block 48 which effectively ends this threat assessment of the potential threat information received by the threat evaluation module 42. If an active threat signal 50 is generated by the threat assessment unit 44 from the data received from the threat evaluation module 42, a threat confirmation request 52 is generated and forwarded to a threat timer unit 54. A confirmation request is visually and audibly presented to the occupants 12 and a predetermined time interval is allowed for one of the occupants 12 to confirm if an active threat is present in the automobile vehicle 11. If the predetermined time interval is not exceeded prior to receiving a response from any of the occupants 12 a time interval not-exceeded signal 56 is generated which initiates operation of a confirmation unit 58. If the confirmation unit 58 receives confirmation from any one of the occupants 12 that no threat is present, a second no-threat signal 60 is generated and saved at the "nothing abnormal" block 48 which effectively ends this threat assessment of the potential threat information received by the confirmation unit 58.

If the predetermined time interval is exceeded prior to receiving a response from any of the occupants 12 a time interval time-out signal 62 is generated and operation of a threat level determination unit 64 is initiated. If the confirmation unit 58 receives the confirmation from any one of the occupants 12 that a threat is present, an active threat signal 66 is generated and forwarded to the threat level determination unit 64. The threat level determination unit 64 applies logic for example from Table 1 and Table 2 below to identify if the active threat should be categorized as one of a "low threat" 68, a "medium threat" 70 or a "high threat" 72. Identification of the "low threat" 68 results in generation of an activation command 74 which activates a vehicle horn and a vehicle warning flasher. Identification of the "medium threat" 70 results in a second activation command 76 which activates the vehicle horn and the vehicle warning flasher as well as activating a vehicle brake assist system and notification of the medium threat 70 to the outside source 43. Identification of the "high threat" 72 results in a third activation command 78 which activates the vehicle horn and the vehicle warning flasher as well as activating the vehicle brake assist system and forwards a request to the outside source 43 to initiate a 911 emergency assistance request.

Referring to FIG. 2 and again to FIG. 1, in addition to the features identified in FIG. 1, the in-vehicle multimodal violence detection system 10 also initially gathers occupant information in an occupant information request 80. An occupant confirmation unit 82 identifies by receipt of a occupant status signal 84 forwarded to the occupant confirmation unit 82 that only a single occupant 12 or passenger is present in the automobile vehicle 11, which does not necessitate further operation of the in-vehicle multimodal violence detection system 10 as no threat will be present. A multiple occupant status signal 86 if generated by the occupant confirmation unit 82 confirms that two or more occupants 12 or passengers are present in the automobile vehicle 11, which may necessitate further operation of the in-vehicle multimodal violence detection system 10. Generation of the multiple occupant status signal 86 actuates operation of a ride type identification unit 88.

If a "hailing ride type" signal 90 is generated by the ride type identification unit 88 a program assumption is made that all of the occupants 12 present in the automobile vehicle 11 are known to each other and that no threats will later occur requiring further operation of the in-vehicle multimodal violence detection system 10. If a "sharing ride type" signal 92 is generated by the ride type identification unit 88 a program assumption is made that at least one of the occupants 12 present in the automobile vehicle 11 is not previously known to other ones of the occupants 12 and that a potential therefore exists for a threat to develop during subsequent operation of the automobile vehicle 11.

The sharing ride type signal 92 is forwarded to the speech and audio event recognition module 16 and to the shaking motion movement module 20. The speech and audio event recognition module 16 receives occupant speech signals from one or more operational microphones 94 of the in-vehicle microphones 14 discussed in reference to FIG. 1. The occupant speech signals are evaluated against saved data to identify if an occupant's speech pattern signifies an abnormal audio event. An abnormal audio event may include but is not limited to a verbal threat against the health or safety of one of the occupants or a sound volume exceeding a predetermined maximum volume threshold. An abnormal audio trigger assessment 96 is performed and if an audio triggering event 98 is negative the program returns to the speech and audio event recognition module 16 for continued audio monitoring. If an audio triggering event 100 is detected and therefore positive the program continues to the picture compilation module 38 and to the heart rate and breathing rate detection module 28.

If the "sharing ride type" signal 92 is generated, in parallel with operation of the speech and audio event recognition module 16 the shaking motion movement module 20 receives accelerometer signals 102 from one or more in-vehicle accelerometers 18 discussed in reference to FIG. 1. The accelerometer signals 102 are evaluated against saved data to identify if accelerometer data signifies an abnormal motion event. An abnormal motion event may include but is not limited to a rapid or intense acceleration or motion of one of the occupants 12 or an acceleration level exceeding a predetermined maximum accelerometer threshold. An abnormal motion trigger assessment 104 is performed and if a motion triggering event 106 is negative the program returns to the shaking motion movement module 20 for continued motion monitoring. If a motion triggering event 108 is detected and therefore positive the program continues to the picture compilation module 38 and to the heart rate and breathing rate detection module 28.

The heart rate and breathing rate detection module 28 receives output radar data 110 from the one or more in-vehicle radar devices 26 whose output data is correlated to heart rates and breathing rates of the occupants 12 discussed in reference to FIG. 1. The output radar data 110 is evaluated against saved data to identify if radar data signifies an abnormal occupant heart rate or breathing rate event. The occupant heart rate or breathing rate event may include but is not limited to a rapid or intense increase of a heart rate or a breathing rate of one of the occupants 12 or a heart rate or breathing rate level exceeding a predetermined maximum heart rate or breathing rate threshold. An abnormal occupant heart rate or breathing rate trigger assessment 112 is performed and if a heart rate or breathing rate triggering event 114 is negative the program returns to the heart rate and breathing rate detection module 28 for continued heart rate and breathing rate monitoring. If a heart rate or breathing rate triggering event 116 is detected and therefore positive the program continues to the picture compilation module 38 and to the in-vehicle semantic scene recognition module 24.

The in-vehicle semantic scene recognition module 24 receives camera signals 118 from multiple in-vehicle cameras 119 as the in-vehicle camera data 22 discussed in reference to FIG. 1 in an image quality assessment module 120 which reviews and adjusts image quality of the received camera signals 118. An initial assessment is made if one or more of the in-vehicle cameras 119 is covered in a camera assessment unit 122. If a camera covered signal 124 is generated one or more of the in-vehicle cameras 119 are covered and therefore are unable to receive images, and an audio pulse signal is generated by the camera assessment unit 122 to notify the occupants 12 of the automobile vehicle 11 to uncover a covered one of the multiple in-vehicle cameras 119, and the program moves to the picture compilation module 38. If a camera un-covered signal 127 is generated at least one or more of the in-vehicle cameras 119 are uncovered and are therefore able to receive images, and the program moves to the in-vehicle semantic scene recognition module 24.

The in-vehicle semantic scene recognition module 24 in a comparator 128 compares image data received from the in-vehicle cameras 119 against a database having images representing "normal" scenes such as occupants 12 seated and moving normally such as during conversation, exiting or entering the automobile vehicle 11. If the in-vehicle camera data 22 compared to the images in the saved database generates a no-abnormal scene signal 130 the program returns to the in-vehicle semantic scene recognition module 24 to continue monitoring. If the in-vehicle camera data 22 compared to the images in the saved database generates the vision-based threat indicators 34 indicating an abnormal scene is present, the program moves to the picture compilation module 38. As noted above with respect to FIG. 1, the picture compilation module 38 communicates with the threat evaluation module 42 to identify potential threats for further analysis and confirmation.

Referring to FIG. 3 and again to FIGS. 1 and 2, according to several aspects, the in-vehicle multimodal violence detection system 10 includes an audio-based event recognition portion 132 which functions in concert with the speech and audio event recognition module 16 described in reference to FIG. 1. When speech of an occupant 12 is detected the audio-based event recognition portion 132 provides communication of audio signals 134 generated by the in-vehicle microphones 14 to a voice activity detection module 136. The voice activity detection module 136 confirms the acoustic signals relate to an acoustic utterance of an occupant 12 which is converted to an acoustic utterance signal 138. The acoustic utterance signal 138 is forwarded to a feature extraction module 140 which extracts feature vectors 142 including Mel-frequency cepstral coefficients (MFCC's), filter-bank energies, logs of the filter-bank energies and spectral sub-band centroids for example using Fourier transform equations.

Figure 3:
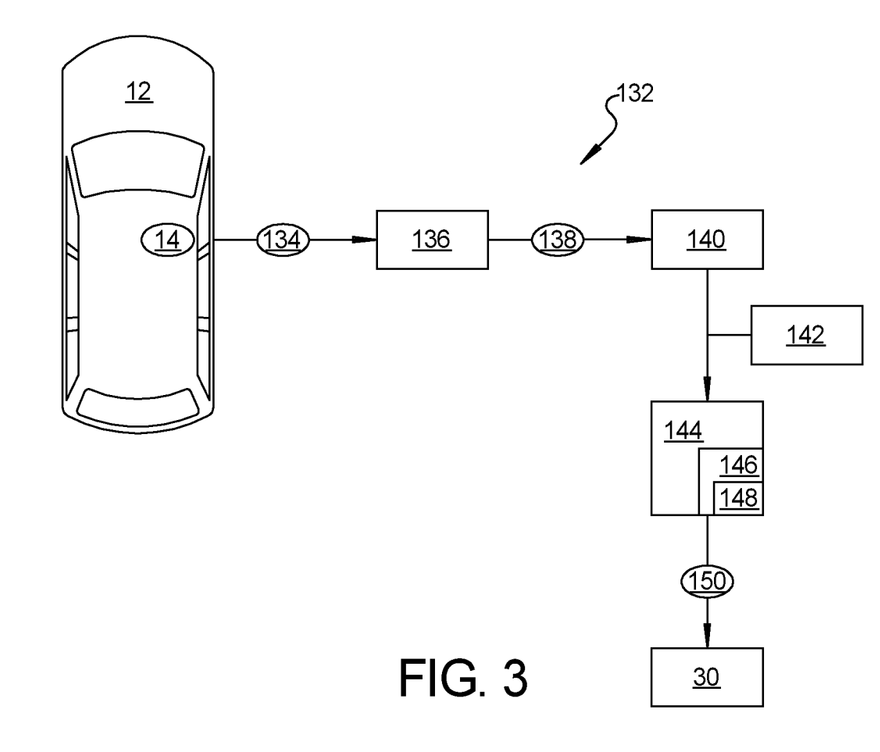
FIG. 3 is a flow diagram of an audio-based event recognition portion of the in-vehicle multimodal violence detection system of FIG. 1.

The feature vectors 142 and similar features from the feature extraction module 140 are forwarded to a speech and non-speech audio event recognition module 144. The speech and non-speech audio event recognition module 144 accesses a memory 146 having exemplary audio data files 148 representing known, normal and threat data saved in the memory 146. Examples of the threat data saved in the audio data files 148 includes but is not limited to screamed words, shouted words, crying sounds, swear words, threats of violence, glass breaking, gunshot sounds, explosions and the like. The feature vectors 142 are compared to the data saved as the audio data files 148 to identify audio patterns 150 representing a threat audio event. If a threat audio event is identified, one or more of the audio-based threat indicators 30 described above in reference to FIG. 1 is generated.

Table 1 below identifies exemplary fused threat estimates assuming that ATI is the audio-based threat indicator, VTI is the vision-based threat indicator, XTI is the vibration-based threat indicator, PTI is the physiological-based threat indicator, and FTE is the fused threat estimate developed from the threat indicators.

TABLE 1

| audio-based threat indictor ATI | vision-based threat indicator VTI | vibration-based threat indicator XTI | physiological-based threat indictor PTI | Fused Threat Estimate FTE |
| --- | --- | --- | --- | --- |
| No Threat | No Threat | No Threat | No Threat | No Threat |
| No Threat | No Threat | No Threat | Threat | Low Threat |
| No Threat | No Threat | Threat | No Threat | Low Threat |
| No Threat | No Threat | Threat | Threat | Low Threat |
| No Threat | Threat | No Threat | No Threat | Medium Threat |
| No Threat | Threat | Threat | Threat | Threat |
| No Threat | Threat | No Threat | Threat | High Threat |
| No Threat | Threat | Threat | No Threat | High Threat |

TABLE 1-continued

| audio-based threat indictor ATI | vision-based threat indicator VTI | vibration-based threat indicator XTI | physiological-based threat indictor PTI | Fused Threat Estimate FTE |
|---|---|---|---|---|
| No Threat | Threat | Threat | Threat | High Threat |
| Threat | No Threat | No Threat | No Threat | Medium Threat |
| Threat | No Threat | No Threat | Threat | High Threat |
| Threat | No Threat | Threat | No Threat | High Threat |
| Threat | No Threat | Threat | Threat | High Threat |
| Threat | Threat | No Threat | No Threat | High Threat |
| Threat | Threat | No Threat | Threat | High Threat |
| Threat | Threat | Threat | No Threat | High Threat |
| Threat | Threat | Threat | Threat | High Threat |

Other approaches can be used to fuse the four indicators such as using a weight scheme that combines the four threat indicators using weights that are inversely proportional, with an uncertainty of each threat indicator quantified using its variance. Another approach is to use Dempster's rule of combination that takes into consideration a degree of belief of each threat indicator.

Table 2 below identifies consolidated threat estimates (CTE) generated using fused threat estimates together with contextual information including a location where the automobile vehicle is located and a time of day.

TABLE 2

| Fused Threat Estimate (FTE) | Contextual Information | | Consolidated Threat Estimate (CTE) |
|---|---|---|---|
| | Location | Time | |
| No Threat | Any | Any | No Threat |
| Low Threat | Safe Area | Normal | Low Threat |
| Low Threat | Safe Zone | Too Early/Too Late | High Threat |
| Low Threat | Dangerous Zone | Normal | High Threat |
| Low Threat | Dangerous Zone | Too Early/Too Late | High Threat |
| High Threat | Safe Area | Normal | High Threat |
| High Threat | Safe Zone | Too Early/Too Late | High Threat |
| High Threat | Dangerous Zone | Normal | High Threat |
| High Threat | Dangerous Zone | Too Early/Too Late | High Threat |

A method for operating the in-vehicle multimodal violence detection system 10 may include the following. The speech and non-speech audio event recognition module 144 recognizes multiple swear and threating words and non-speech audio events such as inarticulate sounds and sounds accompanying threat or abnormal behaviors such as shouting, screaming, crying and glass breaking as audio-based threat indictors. Audio events include, but are not limited to, crying, screaming, shouting, glass breaking, gunshot and explosions. The shaking motion movement module 20 recognizes shaking movements of the occupants 12 using in-vehicle accelerometer data. The heart rate and breathing rate detection module 28 analyzes sudden physiological changes in heart rates and breathing rhythms of the occupants 12. The in-vehicle semantic scene recognition module 24 captures and analyzes the non-verbal interaction between the occupants 12 and if a threat condition is present generates one or more occupant threat indicators. The multimodal threat evaluation module 42 analyzes the situation using the audible, visual, physiological and vibration-based indicators and applies a priori knowledge including a history record of violence and contextual information such as vehicle location, time of the day, and the like to determine the threat level.

The in-vehicle multimodal violence detection system 10 provides detection of one or more covered in-vehicle cameras 119 and alerts the occupants 12 inside the automobile vehicle 11 to uncover the covered one or more of the in-vehicle cameras 119, for example using an audible tone. The in-vehicle multimodal violence detection system 10 automatically detects changes in occupant heartbeat, occupant heart rate and applies this data if required as an occupant threat indicator. Different actions are recommended according to the threat level.

The in-vehicle multimodal violence detection system 10 of the present disclosure provides a system and method for evaluating possible threats for a vehicle driver or occupant, or among un-acquainted occupants or passengers during a shared ride of an autonomous automobile vehicle. The present system includes a non-speech audio event recognition module, an in-vehicle accelerometer-based shaking movement detection module, an in-vehicle semantic scene understanding module and a threat level estimation module. For ride sharing applications the system and method of the present disclosure incorporate ride and rider information from a shared autonomous automobile vehicle booking database and analyze the ride and rider information to recognize threat scenarios between strangers.

An in-vehicle multimodal violence detection system 10 of the present disclosure offers several advantages. These include a system and a method for evaluating possible threats to a vehicle driver or occupant 12 or among strange riders defining the occupants 11 in the shared autonomous automobile vehicle 11. It comprises a non-speech audio event recognition module, an in-vehicle accelerometer-based shaking movement detection module, an in-vehicle semantic scene understanding module and a threat level estimation module. In ride sharing applications the system and method of the present disclosure incorporates ride and rider information from the SAV booking database and analyze it to recognize scenarios between strangers.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. An in-vehicle multimodal violence detection system, comprising:
   a speech and non-speech audio event recognition module capturing threat words and non-speech audio events of occupants of an automobile vehicle;
   multiple in-vehicle accelerometers generating in-vehicle accelerometer data analyzed in a shaking movement recognition module;
   one or more in-vehicle radar devices detecting heart rates and breathing rates of vehicle occupants, the system directing signals from the in-vehicle radar devices to a heart rate and breathing rate detection module, the heart rate and breathing detection module measuring physiological changes in heart rates and breathing rhythms of the occupants and analyzing sudden changes in heart rates and breathing rhythms;

one or more in-vehicle cameras capturing occupant positions and movements over time, the system directing signals from the one or more in-vehicle cameras to an in-vehicle semantic scene recognition module that captures and analyzes non-verbal interactions between the occupants;

one or more occupant threat indicators including an audible threat indicator generated by the speech and non-speech audio event recognition module, a visual threat indicator generated by the in-vehicle semantic scene recognition module, a physiological threat indicator generated by the heart rate and breathing rate detection module and a vibration-based threat indicator generated by the shaking movement recognition module;

a threat level determination unit initiated by a time interval time-out signal if a predetermined time interval is exceeded prior to receiving a response from any one of the occupants;

an active threat signal generated and forwarded to the threat level determination unit if any one of the occupants confirm that an active threat is present;

the threat level determination unit identifying if the active threat should be categorized as one of a "low threat", a "medium threat" or a "high threat", wherein:
identification of the "low threat" activates a vehicle horn and a vehicle warning flasher;
identification of the "medium threat" activates the vehicle horn and the vehicle warning flasher and activates a vehicle brake assist system and notification of the medium threat to an outside source; and
identification of the "high threat" activates the vehicle horn and the vehicle warning flasher, activates the vehicle brake assist system and forwards a request to the outside source to initiate an emergency assistance request.

2. The in-vehicle multimodal violence detection system of claim 1, including a priori knowledge defining a history record of violence applied to determine a threat level.

3. The in-vehicle multimodal violence detection system of claim 2, including an outside source providing the a priori information.

4. The in-vehicle multimodal violence detection system of claim 2, wherein the a priori information includes an area of travel wherein known violence has occurred and a past history record of different "normal" versus "threat" events.

5. The in-vehicle multimodal violence detection system of claim 1, including a picture compilation module identifying vectors combining an output signal from the speech and non-speech audio event recognition module, the shaking movement recognition module, the heart rate and breathing rate detection module and the in-vehicle semantic scene recognition module and assigning predetermined thresholds distinguishing between a normal event and a threat event.

6. The in-vehicle multimodal violence detection system of claim 5, including a threat evaluation module analyzing the threat event using audible, visual, physiological and vibration-based indicators, and an a priori knowledge including a history record of violence and contextual information having a location and a time of day to determine a threat level.

7. The in-vehicle multimodal violence detection system of claim 6, including a threat assessment unit receiving the threat level and confirming if an active threat is present and generating an active threat signal.

8. The in-vehicle multimodal violence detection system of claim 7, wherein after generating the active threat signal a threat confirmation request is generated and forwarded to a threat timer unit.

9. The in-vehicle multimodal violence detection system of claim 8, including:
a confirmation request visually and audibly presented to the occupants and the predetermined time interval allowed for at least one of the occupants to confirm if the active threat is present in the automobile vehicle is set.

10. A method to perform in-vehicle multimodal violence detection, comprising:
capturing threat words and non-speech audio events of occupants of an automobile vehicle using a speech and non-speech audio event recognition module;
analyzing in-vehicle accelerometer data in a shaking movement recognition module;
identifying, with one or more in-vehicle radar devices, sudden physiological changes in heart rates and breathing rhythms of the occupants in a heart rate and breathing rate detection module, the one or more in-vehicle radar devices detecting heart rates and breathing rates of vehicle occupants;
directing signals from the in-vehicle radar devices to the heart rate and breathing rate detection module;
capturing, with one or more in-vehicle cameras, occupant positions and movements over time;
directing signals from the one or more in-vehicle cameras to an in-vehicle semantic scene recognition module;
analyzing, with in-vehicle semantic scene recognition module, non-verbal interactions between the occupants; and
generating one or more occupant threat indicators including audible, visual, physiological and vibration-based indicators, including:
initiating, by a time interval time-out signal, a threat level determination unit if a predetermined time interval is exceeded prior to receiving a response from any one of the occupants;
generating and forwarding an active threat signal to the threat level determination unit if any one of the occupants confirm that an active threat is present;
identifying, by the threat level determination unit, if the active threat should be categorized as one of a "low threat", a "medium threat" or a "high threat", and:
activating a vehicle horn and a vehicle warning flasher upon identification of the "low threat";
activating the vehicle horn and the vehicle warning flasher and activating a vehicle brake assist system and notifying an outside source of the "medium threat" upon identification of the "medium threat"; and
activating the vehicle horn and the vehicle warning flasher, activating the vehicle brake assist system and forwarding a request to the outside source to initiate an emergency assistance request upon identification of the "high threat".

11. The method of claim 10, further including applying a priori knowledge including a history record of violence to determine a threat level.

12. The method of claim 11, further including applying contextual information including a vehicle location and a time of day from the a priori knowledge.

13. The method of claim 10, further including incorporating ride information and occupant information from a booking database and analyzing the ride information and the occupant information to distinguish differences between the occupants.

14. The method of claim 10, further including identifying shaking movements of the occupants of the automobile vehicle using the in-vehicle accelerometer data.

15. The method of claim 10, further including applying inarticulate sounds and sounds accompanying threat or abnormal behaviors including shouting, screaming, crying and glass breaking as audio-based threat indicators.

16. The method of claim 10, further including analyzing the one or more occupant threat indicators in a multimodal threat evaluation module.

17. A method to perform in-vehicle multimodal violence detection, comprising:
  capturing threat words and non-speech audio events of occupants of an autonomous automobile vehicle using a speech and non-speech audio event recognition module;
  analyzing in-vehicle accelerometer data in a shaking movement recognition module;
  measuring, with one or more in-vehicle radar devices, sudden physiological changes in heart rates and breathing rhythms of the occupants in a heart rate and breathing rate detection module, the one or more in-vehicle radar devices detecting heart rates and breathing rates of vehicle occupants, and directing signals from the one or more in-vehicle radar devices to the heart rate and breathing rate detection module;
  capturing, with multiple in-vehicle cameras, occupant positions and movements over time;
  directing signals from the multiple in-vehicle cameras to an in-vehicle semantic scene recognition module;
  analyzing, with the in-vehicle semantic scene recognition module, non-verbal interactions between the occupants;
  generating one or more occupant threat indicators including audible, visual, physiological and vibration-based indicators; and
  identifying vectors combining an output signal from the speech and non-speech audio event recognition module, the shaking movement recognition module, the heart rate and breathing rate detection module and the in-vehicle semantic scene recognition module and assigning predetermined thresholds distinguishing between a normal event and a threat event in a picture compilation module, including
  initiating, by a time interval time-out signal, a threat level determination unit if a predetermined time interval is exceeded prior to receiving a response from any one of the occupants;
  generating and forwarding an active threat signal to the threat level determination unit if any one of the occupants confirm that an active threat is present;
  identifying, by the threat level determination unit, if the active threat should be categorized as one of a "low threat", a "medium threat" or a "high threat", and:
    activating a vehicle horn and a vehicle warning flasher upon identification of the "low threat";
    activating the vehicle horn and the vehicle warning flasher and activating a vehicle brake assist system and notifying an outside source of the "medium threat" upon identification of the "medium threat"; and
  activating the vehicle horn and the vehicle warning flasher, activating the vehicle brake assist system and forwarding a request to the outside source to initiate an emergency assistance request upon identification of the "high threat".

18. The method of claim 17, further including:
  collecting output signals generated by the multiple in-vehicle cameras positioned in the autonomous automobile vehicle;
  identifying if any one of the multiple in-vehicle cameras is covered in a camera assessment unit; and
  generating an audio pulse signal by the camera assessment unit to notify the occupants of the autonomous automobile vehicle to uncover a covered one of the multiple in-vehicle cameras.

19. The method of claim 17, further including:
  identifying by receipt of an occupant status signal forwarded to an occupant confirmation unit if two or more occupants are present in the autonomous automobile vehicle;
  actuating operation of a ride type identification unit, wherein:
  if a "hailing ride type" signal is generated by the ride type identification unit a first program assumption is made that all of the occupants present in the autonomous automobile vehicle are known to each other and that no threats will later occur; or
  if a "sharing ride type" signal is generated by the ride type identification unit a second program assumption is made that at least one of the occupants present in the autonomous automobile vehicle is not previously known to other ones of the occupants and that a potential therefore exists for the threat event to develop during subsequent operation of the autonomous automobile vehicle.

* * * * *